United States Patent [19]

Carson et al.

[11] Patent Number: 4,599,336

[45] Date of Patent: Jul. 8, 1986

[54] DERIVATIVES OF (E)-3-(4-OXO-4H-QUINAZOLIN-3-YL)-2-PROPENAMIDE

[75] Inventors: Matthew Carson, Nutley; Ronald A. Le Mahieu, North Caldwell; William C. Nason, Mountain Lakes; Jefferson W. Tilley, North Caldwell, all of N.J.

[73] Assignee: Hoffmann-La Roche Inc., Nutley, N.J.

[21] Appl. No.: 521,308

[22] Filed: Aug. 8, 1983

[51] Int. Cl.$^4$ .................. A61K 31/505; C07D 401/12
[52] U.S. Cl. .................................. 514/259; 514/242; 514/253; 544/182; 544/284; 544/286
[58] Field of Search ........................ 544/284, 286, 182; 424/251; 514/242, 253, 259

[56] References Cited

U.S. PATENT DOCUMENTS 4,281,127  7/1981  LeMahieu et al. ................ 544/287
4,451,467  5/1984  Ishikawa et al. .................. 544/284

OTHER PUBLICATIONS

Iizuka, et al., "J. Med. Chem.", vol. 24, 1981, pp. 1139–1148.
Tanouchi, et al., "J. Med. Chem.", vol. 24, 1981, pp. 1149–1155.
LeMahieu, et al., "J. Med. Chem.", vol. 26, 1983, pp. 420–425.

Primary Examiner—Glennon H. Hollrah
Assistant Examiner—James H. Turnipseed
Attorney, Agent, or Firm—Jon S. Saxe; Bernard S. Leon; Matthew Boxer

[57] ABSTRACT

Compounds of the formula

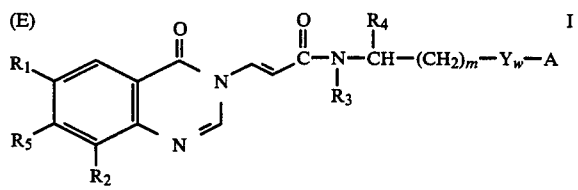

wherein $R_1$ is hydrogen, lower alkyl, lower cycloalkyl, lower alkoxy, hydroxy, halo, lower alkylthio, lower alkylsulfinyl, lower alkylsulfonyl, di-$(C_1-C_7)$ alkyl-$N(CH_2)_nO$— or 2-hydroxyethoxy; n is 2 to 7; $R_2$ is hydrogen, lower alkyl or lower alkoxy; $R_3$ is hydrogen or methyl; $R_4$ is hydrogen or lower alkyl; $R_5$ is hydrogen or lower alkyl provided however if $R_2$ is other than hydrogen $R_5$ is hydrogen; m is 1 to 7; Y is

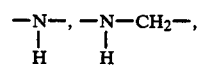

—O— or —S—; w is zero or one; and A is an unsubstituted or substituted aromatic 5- or 6-membered heterocyclic radical;

or pharmaceutically acceptable addition salts thereof are described. The compounds of formula I are useful for treating allergic conditions and vascular disorders.

28 Claims, No Drawings

DERIVATIVES OF (E)-3-(4-OXO-4H-QUINAZOLIN-3-YL)-2-PROPENAMIDE

BRIEF SUMMARY OF THE INVENTION

The invention relates to compounds of the formula

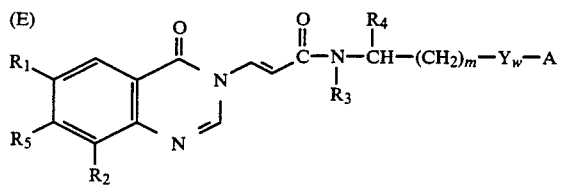

wherein $R_1$ is hydrogen, lower alkyl, lower cycloalkyl, lower alkoxy, hydroxy, halo, lower alkylthio, lower alkylsulfinyl, lower alkylsulfonyl, di-($C_1$-$C_7$)alkyl-N(CH$_2$)$_n$O— or 2-hydroxyethoxy; n is 2 to 7; $R_2$ is hydrogen, lower alkyl or lower alkoxy; $R_3$ is hydrogen or methyl; $R_4$ is hydrogen or lower alkyl; $R_5$ is hydrogen or lower alkyl; provided however if $R_2$ is other than hydrogen $R_5$ is hydrogen; m is an integer of 1 to 7; Y is

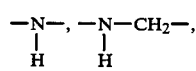

—O—, or —S—; W is zero or one; and A is an unsubstituted or substituted 5- or 6-membered heterocyclic radical;

and pharmaceutically acceptable acid addition salts thereof.

DETAILED DESCRIPTION OF THE INVENTION

As used herein, the term "lower alkyl" denotes a straight- or branched-chain saturated hydrocarbon containing 1 to 7 carbon atoms, for example, methyl, ethyl, propyl, isopropyl, butyl, t-butyl, neopentyl, pentyl, heptyl and the like. The term "lower alkoxy" denotes an alkoxy group in which the lower alkyl group is as described above, for example, methoxy, ethoxy, propoxy, pentoxy, and the like. The term "lower alkylthio" denotes an alkylthio group in which the lower alkyl group is as described above, for example, methylthio, ethylthio, propylthio, pentylthio, and the like. The term "lower alkylsulfinyl" denotes an alkylsulfinyl group in which the lower alkyl group is as described above, for example, methylsulfinyl, ethylsulfinyl, and the like. The term "lower alkylsulfonyl" denotes an alkylsulfonyl group in which the lower alkyl group is as defined above, for example, methylsulfonyl, ethylsulfonyl, and the like. The term "halo" denotes all the halogens, i.e., bromine, chlorine, fluorine, and iodine. Exemplary of di($C_1$-$C_7$)-alkyl—N—(CH$_2$)$_n$—O—groups are dimethylaminoethoxy, diethylaminoethoxy, dipropylaminoethoxy, diisopropylaminobutoxy, dibutylaminoethoxy, dipentylaminoethoxy, or the like. The term "lower cycloalkyl" denotes a cyclic hydrocarbon containing up to 7 carbon atoms, for example cyclopropyl, cyclobutyl, cyclopentyl, cyclohexyl and cycloheptyl.

The term "heterocyclic radical" denotes a 5- or 6-membered hetercyclic ring unsubstituted or substituted, especially hetero-aromatic rings which contain 1 to 3, or particularly 1 or 2, hetero-atoms which may be the same or different. Nitrogen, oxygen and sulfur are the preferred hetero-atoms.

Examples of heterocyclic radicals are pyridyl, pyrimidinyl, imidazolyl, furyl, thiazolyl, oxazolyl, isoxazolyl, pyrazinyl, quinolinyl, isoquinolinyl, quinazolinyl, 1,2,4-triazinyl, benzimidazolyl and pyridazinyl. Preferred examples of heterocyclic radicals are pyridyl, imidazolyl, pyrimidinyl. The heterocyclic radical can be linked to the rest of the compound either directly or through the following moieties: —S—, —O—, —NH—, or- NH—CH$_2$—. More specifically the heterocyclic radical can be as indicated just below.

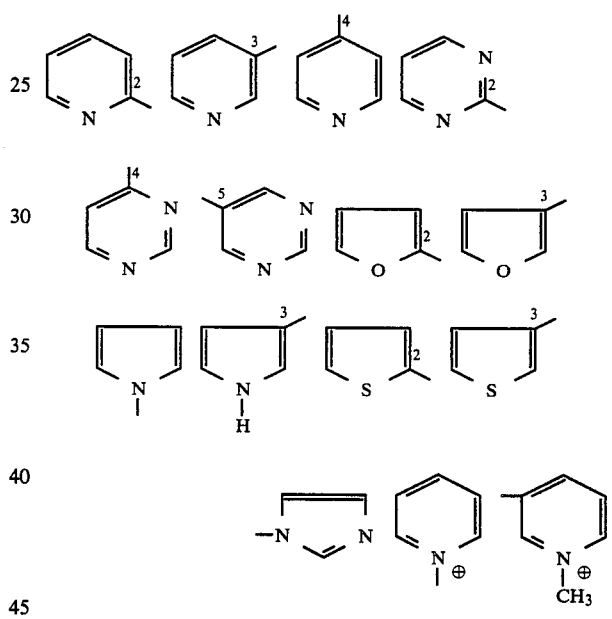

Preferred examples of the heterocyclic radicals of the present invention are as indicated just below.

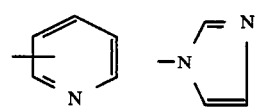

As used herein, the symbol E or (E) designates the stereoisomer of a compound having a trans double bond.

The invention relates to compounds of the formula

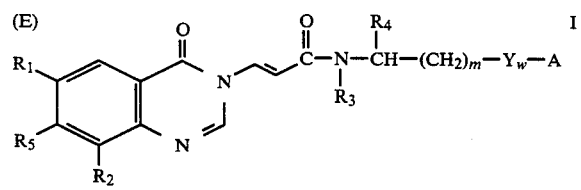

wherein $R_1$ is hydrogen, lower alkyl, lower cycloalkyl, lower alkoxy, hydroxy, halo, lower alkylthio, lower alkylsulfinyl, lower alkylsulfonyl, di-($C_1$-$C_7$)alkyl-$N(CH_2)_n$—O— or 2-hydroxyethoxy; n is 2 to 7; $R_2$ is hydrogen, lower alkyl or lower alkoxy; $R_3$ is hydrogen or methyl; $R_4$ is hydrogen or lower alkyl; $R_5$ is hydrogen or lower alkyl provided however if $R_2$ is other than hydrogen $R_5$ is hydrogen; m is an integer from 1 to 7; Y is

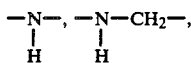

—O—, or —S—; W is zero or 1; an unsubstituted or substituted aromatic 5- or 6-membered heterocyclic radical;

and pharmaceutically acceptable acid addition salts thereof.

In a preferred aspect, the invention comprises compounds of formula I wherein $R_1$ is lower alkyl, most preferably isopropyl; $R_3$ is hydrogen or methyl; $R_4$ is hydrogen and $R_5$ is hydrogen; and A is a -2, -3 or -4-pyridinyl or a 1-imidazolyl substituent.

Examplary of compounds of formula I are:

(E)-3-(4-oxo-4H-quinazolin-3-yl)-N-[4-(3-pyridinyl)-butyl]-2-propenamide;

(E)-3-(4-oxo-4H-quinazolin-3-yl)-N-[4-(2-pyridinyl)-butyl]-2-propenamide;

(E)-3-(4-oxo-4H-quinazolin-3-yl)-N-[4-(3-pyridinyloxy)butyl]-2-propenamide;

N-[4-(1H-imidazol-1-yl)butyl]-(E)-3-(4-oxo-4H-quinazolin-3-yl)-2-propenamide;

(E)-3-(4-oxo-4H-quinazolin-3-yl)-N-[4-(5-pyrimidinyl)-butyl]-2-propenamide;

N[1-methyl-4-(1H-imidazol-1-yl)butyl]-(E)-3-(4-oxo-4H-quinazolin-3-yl)-2-propenamide;

N-[1-methyl-4-(3-pyridyl)butyl]-(E)-3-(4-oxo-4H-quinazolin-3-yl)-2-propenamide;

(E)-3-(6-methyl-4-oxo-4H-quinazolin-3-yl)-N-[4-(3-pyridinyl)butyl]-2-propenamide;

(E)-3-(6-methyl-4-oxo-4H-quinazolin-3-yl)-N-[4-(3-pyridinyloxy)butyl]-2-propenamide;

N-[4-(1H-imidazol-1-yl)butyl]-(E)-3-(6-methoxy-4-oxo-4H-quinazolin-3-yl)-2-propenamide; 2-propenamide;

(E)-3-(6-methoxy-4-oxo-4H-quinazolin-3-yl)-N-[4-(3-pyridinyloxy)butyl]-2-propenamide;

(E)-3-(6-hydroxy-4-oxo-4H-quinazolin-3-yl)-N-[4-(3-pyridinyl)butyl]-2-propenamide;

(E)-3-(6-hydroxy-4-oxo-4H-quinazolin-3-yl)-N-[4-(1H-imidazol-1-yl)butyl]-2-propenamide;

(E)-3-(6-chloro-4-oxo-4H-quinazolin-3-yl)-N-[4-(5-pyrimidinyl)butyl]-2-propenamide;

(E)-3-(6-chloro-4-oxo-4H-quinazolin-3-yl)-N-[1-methyl-4-(3-pyridyl)butyl]-2-propenamide;

(E)-3-[6-(methylthio)-4-oxo-4H-quinazolin-3-yl]-N-[4-(3-pyridinyl)butyl]-2-propenamide;

(E)-3-[6-(methylthio)-4-oxo-4H-quinazolin-3-yl]-N-[4-(3-pyridinyloxy)butyl]-2-propenamide;

(E)-3-[6-(methylsulfinyl)-4-oxo-4H-quinazolin-3-yl]-N-[4-(2-pyridinyl)butyl]-2-propenamide;

N-[4-(1H-imidazol-1-yl)butyl]-(E)-3-[6-(methylsulfinyl)-4-oxo-4H-quinazolin-3-yl]-2-propenamide;

(E)-3-[6-(1-methylethyl)-4-oxo-4H-quinazolin-3-yl]-N-[4-(5-pyrimidinyl)butyl]-2-propenamide;

N-[1-methyl-4-(1H-imidazol-1-yl)butyl]-(E)-3-[6-(1-methylethyl)-4-oxo-4H-quinazolin-3-yl]-2-propenamide;

(E)-3-[6-(1-methylethyl)-4-oxo-4H-quinazolin-3-yl]-N-[2-(4-pyridinyl)ethyl]-2-propenamide;

N-[1-methyl-4-(3-pyridyl)butyl]-(E)-3-[6-(1-methylethyl)-4-oxo-4H-quinazolin-3-yl]-2-propenamide;

(E)-3-[6,8 bis(1-methylethyl)-4-oxo-4H-quinazolin-3-yl]-N-[4-(2-pyridinyl)butyl]-2-propenamide;

(E)-3-[6,8-bis(1-methylethyl)-4-oxo-4H-quinazolin-3-yl]-N-[4-(3-pyridinyloxy)butyl]-2-propenamide;

N-[4-(1H-imidazol-1-yl)butyl]-(E)-3-[6,8-bis(1-methylethyl)-4-oxo-4H-quinazolin-3-yl]-2-propenamide;

(E)-3-[6,8-bis(1-methylethyl)-4-oxo-4H-quinazolin-3-yl]-N-[4-(5-pyrimidinyl)butyl]-2-propenamide;

N-[1-methyl-4-(3-pyridyl)butyl]-(E)-3-[6,8-bis(1-methylethyl)-4-oxo-4H-quinazolin-3-yl]-2-propenamide;

(E)-3-(6,7-dimethyl-4-oxo-4H-quinazolin-3-yl)-N-[4-(3-pyridinyl)butyl]-2-propenamide;

(E)-3-(6,7-dimethyl-4-oxo-4H-quinazolin-3-yl)-N-[4-(2-pyridinyl)butyl]-2-propenamide;

(E)-3-(6,7-dimethyl-4-oxo-4H-quinazolin-3-yl)-N-[4-(3-pyridinyloxy)butyl]-2-propenamide;

(E)-3-(6,7-dimethyl-4-oxo-4H-quinazolin-3-yl)-N-[4-(1H-imidazol-1-yl)butyl]-2-propenamide;

(E)-3-(6,7-dimethyl-4-oxo-4H-quinazolin-3-yl)-N-[4-(5-pyrimidinyl)butyl]-2-propenamide;

In a still more preferred aspect the invention relates to:

(E)-N-methyl-3-[6-(1-methylethyl)-4-oxo-4H-quinazolin-3-yl]-N-[4-(3-pyridinyl)butyl]-2-propenamide;

(E)-3-[6-(1-methylethyl)-4-oxo-4H-quinazolin-3-yl]-N-[4-(2-pyridinyl)butyl]-2-propenamide;

(E)-3-[6-(1-methylethyl)-4-oxo-4H-quinazolin-3-yl]-N-[4-(3-pyridinyloxy)butyl]-2-propenamide hydrochloride;

N-[4-(1H-imidazol-1-yl)butyl]-(E)-3-[6-(1-methylethyl)-4-oxo-4H-quinazolin-3-yl]-2-propenamide;

(E)-3-[6,8(bis(1-methylethyl)-4-oxo-4H-quinazolin-3-yl]-N-[4-(3-pyridinyl)butyl]-2-propenamide hydrochloride;

Reaction Scheme I

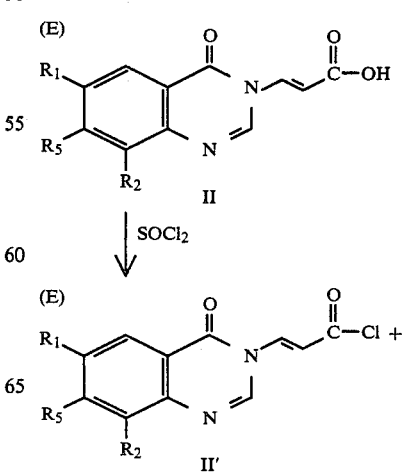

-continued
Reaction Scheme I

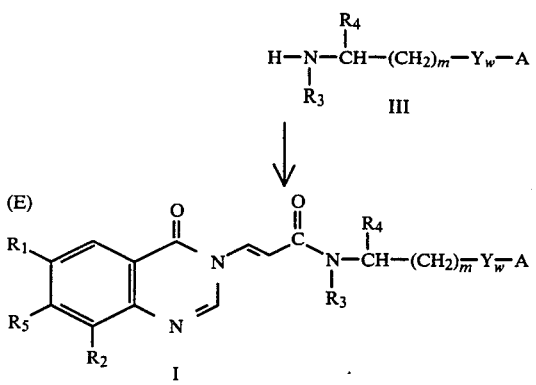

wherein $R_1$, $R_2$, $R_3$, $R_4$, $R_5$, m, w, Y and A are as defined herein.

In Reaction Scheme I, one process for converting the known acids of Formula II to the desired end products of formula I is shown. In this process the compound of Formula II is converted to the corresponding acid chloride II' by reaction with thionyl chloride at elevated temperatures, most preferably at reflux and then treated with an amine of Formula III to yield the desired end product of Formula I. The reaction of the acid chloride with the amine of Formula III may be conveniently carried out in the presence of an inert solvent such as dimethylformamide, or an aromatic hydrocarbon such as toluene. A temperature in the range of from about 0° C. to the reflux temperature of the medium may be employed, the specific temperature in each case being selected depending upon the nature of the amine reactant. Most preferably anhydrous conditions are utilized.

Reaction Scheme II

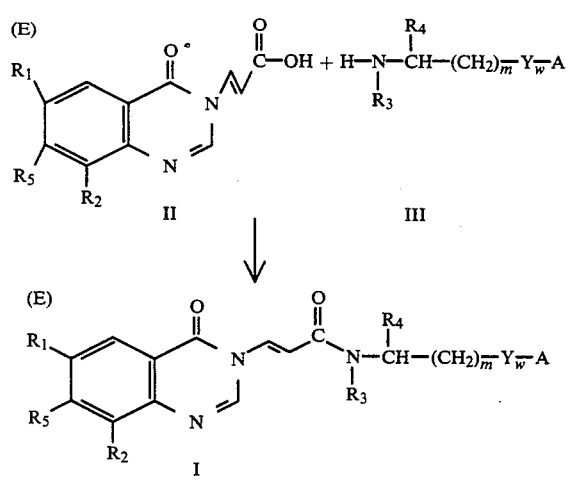

wherein $R_1$, $R_2$, $R_3$, $R_4$, $R_5$, m, w, Y and A are as defined herein.

In Reaction Scheme II, the acids of formula II can be directly coupled to the desired amines of formula III by utilizing the diphenylphosphoryl azide method. In Reaction Scheme II, the reactants are dissolved in a suitable inert solvent, i.e., anhydrous DMF, with cooling to a temperature of about −5° to −20° C. The diphenylphosphoryl azide is added dropwise and then a trialkylamine, preferably triethylamine, is added. Workup of the reaction mixture and isolation of the desired end products of formula I is carried out in a manner known per se.

Examples of acids of Formula II include:
(E)-3-[6-(1-methylethyl)-4-oxo-4H-quinazolin-3-yl]-2-propenoic acid; and
(E)-3-[6,8-bis-(1-methylethyl)-4-oxo-4H-quinazolin-3-yl]-2-propenoic acid.

Examples of compounds of Formula III include:
2-pyridine-1-butanamine;
3-pyridine-1-butanamine;
N-methyl-3-pyridine-1-butanamine;
4-(3-pyridyloxy)-1-butanamine;
(1H-imidazol-1-yl)-1-butanamine;
2-(4-pyridylthio)-1-ethanamine;
3-pyridine-1-hexanamine; and
N-(3-pyridinylmethyl)-1,2 ethandiamine.

Amines which fall into the general class of 2- or 3-pyridine-1-alkanamines can be conveniently prepared from corresponding 2- or 3-pyridine-1-alkanenitriles by hydrogenation in a polar solvent such as methanol or ethanol over Raney Cobalt at high temperatures and pressures. This reaction is followed by known work-up procedures for isolating the resultant 3-pyridine-1-alkanamines. The starting nitriles- that is, the 2- or 3-pyridine-1-alkanenitriles are prepared by first passing an inert gas such as argon or neon through a solution of 3-halopyridine and the appropriate alkynyl nitrile in dry triethylamine to which are added small amounts of bis(triphenylphosphine)palladium dichloride and cuprous iodide. Then work up and isolation of the alkynyl-nitrile appropriate for the next step is conducted. In example 18 are contained specific procedures for preparation of 3-pyridine-1-hexanamine.

Amines which fall into the general class of pyridyloxyalkanamines can be conveniently prepared by the displacement of the halide from an appropriate haloalkylnitrile with an appropriate arylhydroxy compound in the presence of a reagent such as sodium hydride. This reaction is carried out in a polar nonaqueous solvent such as DMF at an initial temperature of about 0° C. to about room temperature to form the resultant aryloxyalkylnitrile which is then reduced to the corresponding aryloxyalkylamine by treatment with an appropriate reducing agent such as lithium aluminum hydride at a temperature of about 0° C. to reflux. Work up and isolation of the desired aryloxyalkylamine are carried out in a usual manner. In Example 5 are contained specific procedures for making 4-(3-pyridinyloxy)-1-butanamines.

Amines which fall into the general class of arylthioalkanamines can be conveniently prepared by reacting an appropriate mercaptoalkanamine with an appropriate halo-substituted aryl compound in a polar protic solvent such as propanol or more preferrably ethanol under an inert atmosphere such as nitrogen or more preferably argon, at a approximately 0° C. to about room temperature for a period of about 1 to about 4 hours. The reaction mixture is then worked up in the usual manner to isolate the desired arylthioalkanamine.

Amines which fall into the general class of (1H-imidazol-1-yl)alkanamines are conveniently prepared by hydrogenating an appropriate (1H-imidazol-1-yl)-alkan nitrile, with a catalyst, preferably Raney-Cobalt, in a polar solvent, such as, for example, a mixture of triethylamine and methanol, under conditions of high temperature 80°–120° C., and high hydrogen pressure (about 800 to about 1200 lbs. hydrogen pressure). The resultant is the desired (1H-imidazol-1-yl)alkanamine. Said (1H-imidazol-1-yl)alkanamine can be isolated by usual procedures such as evaporation of solvent. Example 7 contains specific procedures for making (1H-imidazol-1-yl)butanamine.

The N(-aryl)-1, 2(or 3)-alkandiamines are known compounds or can be prepared according to known procedures.

The compounds of formula I above are basic compounds which form acid addition salts with inorganic or organic acids. More particularly, the compounds of formula I form, with pharmaceutically acceptable organic or inorganic acids, pharmaceutically acceptable acid addition salts, for example, hydrohalides such as hydrochloride, hydrobromide or hydroiodide, other mineral acids salts such as sulfate, nitrate, phosphate or the like, alkyl- and mono-aryl sulfonates such as ethanesulfonate, toluenesulfonate, benzenesulfonate, or the like, other organic acid salts such as acetate, tartrate, maleate, citrate, benzoate, salicylate, ascorbate, or the like. Non-pharmaceutically acceptable acid addition salts of the compounds of formula I above can be converted into pharmaceutically acceptable acid addition salts via conventional metathetic reactions whereby the non-pharmaceutically acceptable anion is replaced by a pharmaceutically acceptable anion; or alternatively, by neutralizing the non-pharmaceutically acceptable acid addition salt and then reacting the so-obtained free base with a reagent yielding a pharmaceutically acceptable anion.

The compounds of formula I, including their salts, are antagonists of bronchoconstriction induced by slow reacting substance of anaphylaxis (SRS-A) as well as inhibitors of its synthesis. Accordingly the compounds of formula I including their salts, are useful for the treatment of certain allergic conditions such as asthma. In addition, the compounds of formula I, including their salts, inhibit the production of thromboxane $A_2$ through the inhibition of thromboxane synthase. Accordingly, the compounds of formula I, including their salts, are useful as agents for the treatment of allergic conditions which include skin afflictions, hay fever, chronic bronchitis, obstructive airways diseases such as asthma, allergic conditions of the eye, and allergic conditions of the gastro intestinal tract, such as food allergies and the treatment of vascular disorders, such as, arrhythmias or the like.

The useful antiallergic activity and antiarrhythmic activity of the compounds of formula I including their salts, can be demonstrated in vitro and in warm-blooded animals utilizing standard procedures. Exemplary of such procedures are:

(a) Guinea Pig Ileum, In Vitro

The guinea pig ileum bioassay system has been described by Orange and Austen, Adv. Immunol. 10: 104–144 (1959). A 1.5 cm segment is removed from animals weighing 300–400 g. and suspended in an organ bath containing 10 ml. of Tyrodes solution with $10^{-6}M$ atropine sulfate and $10^{-6}M$ pyrilamine maleate. The bath is maintained at 37° C. and aerated with a mixture of 95% oxygen and 5% carbon dioxide. The SRS-A utilized in this screen is obtained by challenging chopped lung fragments from actively sensitized guinea pigs with egg albumin, in vitro. A dose-response curve to SRS-A challenge is established for the ileum. The dose of SRS-A which gives 50% of the maximal contraction ($EC_{50}$) is then used for subsequent challenge. The drug concentration which inhibits, by 50%, the SRS-A-induced constriction of the guinea pig ileum is determined. In this bioassay system the standard SRS-A antagonist, 7-[3-(4-acetyl-3-hydroxy-2-propylphenoxy)-2-hydroxypropoxy]-4-oxo-8-propyl-4H-1-benzopyran-2-carboxylic acid, has an $IC_{50}$ of $3.5 \times 10^{-8}M$. Results obtained with representative compounds of the present invention in this assay are summarized hereafter in Table I.

(b) Guinea Pig Bronchoconstriction, In Vivo

Male guinea pigs (Hostley strain) weighing 300 to 450 grams are anesthetized with urethane (2 g/Kg) intraperitoneally and a polyethylene cannula is inserted into the jugular vein for intravenous drug administration. Tracheal pressure is recorded from a cannula inserted in the trachea and connected to a Statham pressure transducer. Respiration is paralyzed with succinyl choline (1.2 mg/kg, i.v.) and the animals are mechanically respirated (Howard rodent respirator) at 40 breaths/minute and 2.5 cc tidal volume. Two minutes thereafter, propranolol (0.1 mg/kg, i.v.) is administered. Five minutes later, the animals are pretreated intravenously for 30 seconds (at 10 mg/kg) with test drug or control vehicle. The animals are subsequently challenged with a maximally constrictory dose of leukotriene $E_4$ also administered intravenously. The change (cm $H_2O$) between pre and peak ventilatory pressure readings is averaged for three control animals and five drug treated animals. The percent inhibition is calculated from the following formula:

$$\frac{Control - Drug\ Treated}{Control} \times 100.$$

For determination of oral activity, spontaneously breathing animals are pretreated orally for 2 hours (at 100 mg/kg) prior to challenge with leukotriene $E_4$. 7-[2-(4-Acetyl-3-hydroxy-2-propylphenoxy)-2-hydroxypropoxy]-4-oxo-8-propyl-4H-1-benzopyran-2-carboxylic acid elicits a 98% inhibition at 10 mg/kg, i.v., but is orally inactive in this test. Representative compounds of the present invention, i.e., (E)-3-[6-(1-methylethyl)-4-oxo-4H-quinazolin-3-yl]-[4-(3- pyridinyl)butyl]-propenamide hydrochloride and (E)-3-[6,8-bis(1-methylethyl)-4-oxo-4H-quinazolin-3-yl]-N-[4-(3-pyridinyl)butyl]-2-propenamide hydrochloride, both caused a 96% inhibition on i.v. administration. When tested orally in this assay the two compounds of the invention were active, at 100 mg/kg., exhibiting 58±7% and 60±9% inhibition respectively.

(c) Rat Skin Permeability, In Vivo

In this model the ability of $LTE_4$ to increase vascular permeability in rat skin was utilized. Anesthetized rats pretreated for 30 minutes with an antihistamine, pyrilamine maleate, (50 mg/kg i.p.) and a serotonin antagonist, methylsergide maleate (4 mg/kg i.p.), were injected intradermally with a dose of $LTE_4$ which gave a maximum wheal response (in 0.05 ml saline). After introduction of test drug (at 10 mg/kg, i.v.) the animals were immediately treated intravenously with Evans blue dye i.v. (0.5%) in the tail vein resulting in the formation of a skin wheal. Thirty minutes later the animals were sacrificed and the skin wheal size was measured. The average response in 5 animals (4 intradermal injections per animal) treated with test compound was compared to that obtained in a similar group of control animals to determine the percent inhibition by the drug.

In this test representative compounds of the present invention, i.e., (E)-3-[6-(1-methylethyl)-4-oxo-4H-quinazolin-3-yl]-N-[4-(3-pyridinyl)butyl]-2-propenamide hydrochloride (Compound A), (E)-3-[6,8-bis-(1-methylethyl)-4-oxo-4H quinazolin-3-yl]-N-[4-(3-pyridinyl)butyl]-2-propenamide hydrochloride (Compound B) and N-[4-(1H-imidazol-1-yl)butyl]-(E)-3-[6-(1-methylethyl)-4-oxo-4H quinazolin-3-yl]-2-propenamide (Compound C), gave $I.D._{50}$ of 9.9, 10 and 17 mg/kg i.v., respectively. The standard compound, 7-[3-(4-acetyl-3-hydroxy-2-propylphenoxy)-2-hydroxypropoxy]-4-oxo-8-propyl-4H-1-benzopyran-2-carboxylic acid, caused an 88% reduction in the wheal size at 10 mg/kg i.v. When tested orally in this assay, Compounds A and C were also active giving $I.D._{50}$ of 64, and 96 mg/kg p.o., respectively, while the standard compound was inactive.

(d) Thromboxane Synthase Inhibition, In Vitro $TXA_2$ synthase activity is measured by following the conversion of $^{14}C$-prostaglandin endoperoxide ($PGH_2$) to $^{14}C$-thromboxane $A_2$ ($TXA_2$) using microsomal fractions from human platelets as enzyme source. In the aqueous incubation medium, the $TXA_2$ decomposes rapidly into $TXB_2$. The amount of $TXA_2$ synthase is adjusted so that under the conditions of the assay approximately 80–90% of the substrate, $PGH_2$, is converted to product in control tubes. To prepare $^{14}C$—$PGH_2$, $^{14}C$—AA (50–60 mCi/mmole; Rose Chem.) is incubated with sheep seminal vesicular gland microsomes for 1.5 minutes at 37° C. and then the $^{14}C$—$PGH_2$ is extracted with diethylether, purified on columns of Sephadex LH-20 or silicic acid, and stored in acetone at −70° C. Incubations are done as follows. Sufficient $^{14}C$—$PGH_2$ to yield a final substrate concentration of 10 μM (30,000 cpm) is added to the incubation tubes and then the acetone is removed under nitrogen. The tubes are placed in an ice bath and then 215 μl of ice cold phosphate buffered saline, 10 μl of ethanol (control) or of test drug in ethanol, and 25 μl of the microsomal suspension are added with mixing in that order as rapidly as possible. The tubes are incubated at 22° C. for 2 minutes, the reaction is stopped and then the radioactive products and the uncoverted $PGH_2$ are extracted and analyzed by thin layer chromatography. The amount of $^{14}C$—$PGH_2$ converted to products is used as analyzed by thin layer chromatography. The amount of $^{14}C$—$PGH_2$ converted to products was used as a measure of $TXA_2$ synthase activity. Inhibitors were tested initially at a final concentration of 100 μM. Results obtained with representative compounds of the present invention in this assay are summarized hereafter in Table I.

(e) $\Delta^5$-Lipoxygenase Inhibition $\Delta^5$-Lipoxygenase inhibition was measured by following the conversion of $^{14}C$-arachidonic acid to $^{14}C$-5-HETE, using rat basophil leukemia cells (RBL-1 cells) as the enzyme source. These cells were maintained in stationary stock cultures and grown in spinner cultures prior to isolation by centrifugation at 4° C. at 1,500×g for 10 minutes. The cells were washed three times at 4° C. with 0.05M Tris HCl (ph 7.2) containing 1 mM EDTA, 14 μM indomethacin and 0.9% NaCl. They were then homogenized at 0°–4° C. using a glass/glass homogenizer in 0.05M Tris-HCl (pH 7.2) containing 1 mM EDTA and 14 μM indomethacin. The homogenate was then centrifuged at 49,300×g for 20 minutes (0°–4° C.) and the resulting supernatant frozen in small aliquots in a dry ice/acetone bath prior to storage at −80° C. Under these conditions, the enzyme was stable to freezing and thawing and to preincubation for 10 minutes at 30° C.

For enzyme assay, 100–200 μl of enzyme was incubated in the presence and absence of test compound (prepared in DMSO) for 10 minutes at 30° C. in 0.05M Tris-HCl buffer (pH 7.2) containing 1 mM glutathione, 2 mM $CaCl_2$, 14 μM indomethacin and 0.25 and 0.5 mM EDTA (final volume 400 μl). The final DMSO concentration in these assays was 4%. The assay was initiated by the addition of 100 μl $^{14}C$-arachidonic acid (58 mCi/mmole) and incubations were carried out for 10 minutes at 37° C. in a shaking water bath. The reactions were stopped by the simultaneous addition of 4.0 ml of diethylether and 100 μl of 1.0 m citric acid, while the tubes were vigorously vortexed. The $^{14}C$-5-HETE generated by the enzyme was extracted into the acidified ether layer which was separated from the aqueous layer by freezing the assay tubes in a dry ice/acetone bath prior to decanting the liquid ether layer. The ether layer was evaporated to dryness under $N_2$, the residue dissolved in 65 μl chloroform:methanol (2:1 v/v), prior to separating $^{14}C$-5-HETE from other $^{14}C$-labeled compounds on silica gel impregnated glass fiber TLC plates utilizing an elution solvent of isoctane:methylethylketone:acetic acid (100:9:1 v/v). $^{14}C$-5-HETE was identified by its co-chromatography with a chemically synthesized standard. The radioactive peaks of the chromatogram were cut out and the radioactivity was quantitated by liquid scintillation counting. The amount of 5-HETE obtained per sample was expressed as the percent of total and was calculated in the basis of:

$$\frac{\text{amount of }^{14}\text{C in 5HETE peak}}{\text{amount of total }^{14}\text{C chromatographed}} \times 100$$

in order to evaluate the effect of the test compounds, the mean percent inhibition of $^{14}$C-5-HETE production was calculated. The IC$_{50}$ for a drug was determined from a linear regression analysis of a plot of the mean percent inhibition vs drug concentration.

Results obtained with representative compounds of the present invention in this assay are summarized hereafter in Table I.

(f) PAF Radioreceptor Binding Assay

Platelet rich plasma is prepared by centrifugation of citrate-treated dog blood. Acidification to pH 6.5 with 0.15M citric acid and centrifugation for 10 minutes at 1000 g yields a platelet pellet which is then washed by resuspension in EDTA-Phosphate Buffered Saline (PBS) and recentrifuged. The washed platelet preparation is adjusted to $2 \times 10^7$ platelets/50 μl in 0.1% BSA-PBS.

To a 400 l microfuge tube containing 50 μl silicone oil (specific gravity 1.023) is added buffer, PAF standard or analog, or an extract to bring the aqueous volume to 150 μl. 50 μl of $^3$H-PAF (10,000 cpm, 45 Ci/mM) is added followed by $2 \times 10^7$ dog platelets. After mixing, incubating for 10 minutes at room temperature, and centrifuging for 1 minute in a Beckman Microfuge B (8000 g), the pellet is removed by clipping off the tip of the tube, solubilizing the platelets with 200 μl of 50% methanol, and counting in 10 ml of Aquasol. A curve of 50–2500 pg/tube is obtained within 10 minutes of incubation which demonstrates high specificity and correlation with biological activity for PAF and its analogs. Results obtained with representative compounds of the present invention in this assay are summarized hereinafter in Table I.

(g) In Vivo Screening Procedure for SRS-A Synthesis Inhibitors in Guinea Pigs

Paralyzed, artifically ventilated, actively sensitized guinea pigs are pretreated with indomethacin (to divert the flow of endogenous arachidonic acid through the lipoxygenase pathway), pyrilamine maleate (to block any bronchoconstriction due to released histamine) and propanol (to enhance the sensitivity of the guinea pig bronchoconstriction to SRS-A) prior to challenging the animal with antigen. Under these conditions the resulting antigen-induced bronchoconstriction has been characterized as being attributable to the synthesis and release of SRS-A in the guinea pig lung. Test compounds are initially studied for their inhibitory properties in this test system by the intravenous route (at 10 mg/kg). Results for representative compounds are shown in Table II.

TABLE I

Anti SRS-A Activity, TXA$_2$ Synthase Inhibition, Δ$^5$-Lipoxygenase Inhibition and PAF Binding Activity

| R | R$_2$ | Guinea Pig Ileum, IC$_{50}$ (M) | TXA$_2$ Synthase Inhibition (% at $10^{-7}$ M) | Δ$^5$-Lipoxygenase Inhibition (% at $10^{-5}$ M) | PAF Binding IC$_{50}$, M |
|---|---|---|---|---|---|
| NH(CH$_2$)$_4$-pyridyl | H | $1 \times 10^{-6}$ | 48 | 84 (27 at $10^{-6}$ M) | $0.65 \times 10^{-6}$ |
| NH(CH$_2$)$_4$-pyridyl, CH$_3$ | H | $1 \times 10^{-5}$ | 48 | — | — |
| NH(CH$_2$)$_4$O-pyridyl | H | 44% at $10^{-5}$ M | 70 | — | $>10^{-6}$ |
| NH(CH$_2$)$_4$-N(imidazole) | H | $5 \times 10^{-6}$ | 72 | (0 at $10^{-5}$ M) | $>10^{-6}$ |

TABLE I-continued

Anti SRS-A Activity, TXA$_2$ Synthase Inhibition, Δ$^5$-Lipoxygenase Inhibition and PAF Binding Activity

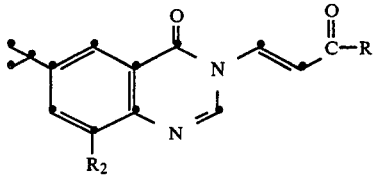

| R | R$_2$ | Guinea Pig Ileum, IC$_{50}$ (M) | TXA$_2$ Synthase Inhibition (% at 10$^{-7}$ M) | Δ$^5$-Lipoxygenase Inhibition (% at 10$^{-5}$ M) | PAF Binding IC$_{50}$, M |
|---|---|---|---|---|---|
| NH(CH$_2$)$_2$S—<pyridyl> | H | 1 × 10$^{-5}$ | 31 | 56 | — |
| NH(CH$_2$)$_4$—<pyridyl> | H | >10$^{-5}$ | >10$^{-5}$ | 100 (IC$_{50}$ = 0.8 × 10$^{-6}$ M) | >10$^{-6}$ |
| NH(CH$_2$)$_2$NHCH$_2$—<pyridyl> | H | 8 × 10$^{-6}$ | 33 at 10$^{-6}$ M | — | — |
| NH(CH$_2$)$_3$NH—<pyridyl> | H | 5 × 10$^{-6}$ | — | 10 | >10$^{-6}$ |
| NH(CH$_2$)$_6$NH—<pyridyl> | H | 5 × 10$^{-6}$ | — | 25 | — |
| NH(CH$_2$)$_6$—<pyridyl> | H | — | — | — | >10$^{-6}$ |
| NH(CH$_2$)$_4$—<pyridyl> | isopropyl | 1 × 10$^{-6}$ | 51 | — | — |

A dash indicates the compound was not tested.

TABLE II

The Effect of Δ$^5$-Lipoxygenase Inhibitor (10 mg/kg iv) in SRS-A Biosynthesis (in Vivo)

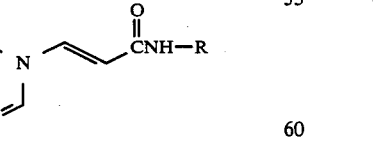

| R | % Inhibition SRS-A Biosynthesis |
|---|---|
| (CH$_2$)$_4$—<2-pyridyl> | 59 |

TABLE II-continued

The Effect of Δ$^5$-Lipoxygenase Inhibitor (10 mg/kg iv) in SRS-A Biosynthesis (in Vivo)

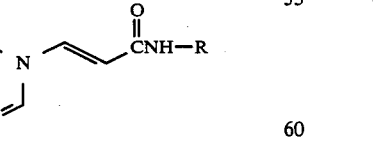

| R | % Inhibition SRS-A Biosynthesis |
|---|---|
| (CH$_2$)$_2$—<4-pyridyl> | 57 |

TABLE II-continued

The Effect of Δ⁵-Lipoxygenase Inhibitor (10 mg/kg iv) in SRS-A Biosynthesis (in Vivo)

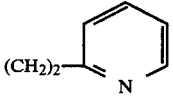

| R | % Inhibition SRS-A Biosynthesis |
|---|---|
| (CH₂)₂-[pyridine] | 56 |

(h) Leukotriene D₄(LTD₄)Induced Arrhythmias in Conscious Guinea Pigs

Male Hartley guinea pigs are anesthetized with sodium pentobarbital and prepared for monitoring direct blood pressure and injecting drugs intravenously by catheterizing the right carotid artery and right jugular vein. Blood pressure, heart rate, and Lead II ECG are monitored in the conscious animal 24 hours later.

Intravenous administration of LTD₄ (2.5 μg/kg) is associated with an increase in blood pressure lasting approximately 1–2 minutes followed by a decrease lasting approximately 5–15 minutes. Abnormal beats consisting of premature ventricular contractions, ST elevation or depression, atrioventricular conduction block, or dissociated p waves begin during the rise in blood pressure; the peak effect occurs approximately 40 seconds after LTD₄. The percent of abnormal beats was quantitated by determining the number present during the first 2 minutes after injection and calculating the percent increase above the control level. During the hypotensive response, the animal usually collapses during the 2nd or 3rd minute after LTD₄ and regains posture approximately 10 minutes after LTD₄.

Test compounds were administered 5 minutes before the LTD₄ challenge and effects on blood pressure and arrhythmias were monitored.

Results obtained with representative compounds of the present invention in this assay are summarized hereafter in Table III.

TABLE III

The Effect of Selected Compounds (10 mg/kg iv) on Blood Pressure and Arrhythmias Induced by LTD₄

| R | Peak Hypertension (Δmm Hg) | Peak Hypotension Δmm Hg | % Arrhythmias |
|---|---|---|---|
| Saline (Control) | 30 ± 4 | −45 ± 4 | 33 ± 4 |
| (CH₂)₄-[pyridine].HCl | 21 ± 6 | −45 ± 4 | 1 ± 1 |
| (CH₂)₄O-[pyridine].HCl | 19 ± 7 | −42 ± 9 | 0 ± 0 |
| (CH₂)₄-N[morpholine-N].HCl | 10 ± 0 | −45 ± 8 | 0 ± 3 |

The compounds of formula I and their pharmaceutically acceptable salts can be administered orally or parenterally as anti-allergic agents, for example, in the prophylactic treatment of bronchial asthma, with dosage adjustments for individual requirements. They can be administered therapeutically, for example, orally or parenterally, by incorporating a therapeutic dosage in a conventional dosage form, such as tablets, capsules, elixirs, suspensions, solutions or the like. They can be administered in mixture with conventional pharmaceutical carriers or excipients, such as, for example, corn starch, calcium stearate, magnesium carbonate, calcium silicate, dicalcium phosphate, talc, lactose, and the like. Moreover, they can be administered in the presence of buffers, or agents used to adjust to isotonicity and the pharmaceutical dosage forms can, if desired, be subjected to conventional pharmaceutical expedients such as, for example, sterilization. As stated above, the dosage can be adjusted to individual requirements. They can also contain other therapeutically valuable substances.

The frequency with which any such dosage form will be administered to a mammal will vary, depending upon the quantity of active medicament present therein and the needs and requirements of the mammal. Dosages of a compound of formula I and its pharmaceutically acceptable salts contemplated for use in practicing the invention are in the range of from about 100 to about 1500 mg per day, either as a single dose or in divided doses. It is to be understood, however, that the above description and dosage strengths and the tablet and capsule descriptions set forth herein are exemplary only and that they do not, to any extent, limit the scope or practice of this invention.

The Examples which follow further illustrate the invention. All temperatures are stated in degrees Centigrade unless otherwise mentioned.

EXAMPLE 1

(E)-3-[6-(1-methylethyl)-4-oxo-4H-quinazolin-3-yl]-2-propenoic acid

A mixture of 30.1 g. (0.16 mol) of 6-(1-methylethyl)-quinazolin-4(3H)-one, 21.2 g. (0.18 mol) of (Z)-3-chloro-2-propenoic acid methyl ester and 33.2 g. (0.24 mol) of anhydrous potassium carbonate in 375 ml. of anhydrous acetone was stirred at reflux for 22 hr. The solvent was removed in vacuo, water was added to the solid residue and the solid was removed by filtration. Recrystallization from methanol gave 35.5 g, m.p. 142°–145°, (82% yield) of (E)-3-[6-(1-methylethyl)-4-oxo-4H-quinazolin-3-yl]-2-propenoic acid methyl ester.

To the above methyl ester (35.5 g.) in 300 ml. of hot acetic acid was added 300 ml. of 6N HCl and the resultant solution was refluxed for 20 minutes. Water (4 L) was added and after cooling the light yellow solid was filtered and washed well with water. After drying, 25.9 g, m.p. 242°–243°, (77% yield) of the above captioned product was obtained.

EXAMPLE 2

(E)-3-[6,8-bis-(1-methylethyl)-4-oxo-4H-quinazolin-3-yl]-2-propenoic acid

A mixture of 3.10 g (0.013)mol) of 6,8-bis-(1-methylethyl)-quinazolin-4(3H)-one, 1.78 g (0.0148 mol) of (Z)-3-chloro-2-propenoic acid methyl ester and 3.72 g (0.027 mol) of anhydrous potassium carbonate in 100 ml. of anhydrous acetone was stirred at reflux for 17 hr. The reaction mixture was filtered, the solid was washed with acetone and the filtrate was concentrated in vacuo to an oil which soon crystallized. Recrystallization from methanol gave 3.11 g, m.p. 102°–103°, (74% yield) of (E)-3-[6,8-bis-(1-methylethyl)-4-oxo-4H-quinazolin-3-yl]-2-propenoic acid methyl ester.

The above methyl ester (3.11 g) was suspended in 75 ml. of 6N HCl and stirred in a preheated oil bath. Reflux temperature was reached in 3 minutes and was maintained for 20 minutes. Water was added, the mixture was cooled and the resultant solid was filtered. Recrystallization from methylene chloride-hexane gave 1.19 g, m.p. 181°–182°, (40% yield) of the above captioned product.

EXAMPLE 3

(E)-3-[6-(1-methylethyl)-4-oxo-4H-quinazolin-3-yl]-N-[4-(3-pyridinylbutyl]-2-propenamide hydrochloride A mixture of 2.58 g. (0.01 mol) of (E)-3-[6-(1-methylethyl)-4-oxo-4H-quinazolin-3-yl]-2-propenoic acid and 25 ml. of thionyl chloride was stirred at reflux for 90 minutes. The excess thionyl chloride was removed in vacuo to yield the acid chloride as a solid which was dissolved in 45 ml. of anhydrous DMF. This solution was stirred at 25° during the dropwise addition of 3.00 g. (0.02 mol) of 3-pyridine butanamine [E. M. Hawes and H. L. Davis, J. Hetero. Chem., 10, 39(1973)] in 20 ml. of anhydrous DMF over 15 minutes. Stirring at 25° was continued for 17 hours and then the solution was concentrated in vacuo to remove the DMF. The residue was dissolved in $CH_2Cl_2$, washed with saturated $NaHCO_3$ solution, washed with water, dried ($Na_2SO_4$) and the $CH_2Cl_2$ was removed in vacuo. The dark solid residue was purified by liquid chromatography using a solvent mixture of 10% $CH_3OH$—$CH_2Cl_2$ to give 2.31 g. of a solid. This was dissolved in $CH_2Cl_2$ and converted to the hydrochloride salt by the addition of 2.4 ml. of 5N HCl in methanol. The solvent was removed in vacuo and the residue was crystallized from 2-propanol to yield 2.31 g. (53% yield), m.p. 187°–188°, of the above-captioned product.

EXAMPLE 4

(E)-N-methyl-3-[6-(1-methylethyl)-4-oxo-4H-quinazolin-3-yl]-N-[4-(3-pyridinyl)butyl]-2-propenamide hydrochloride To a stirred suspension of 2.066 g. (0.008 mol) of (E)-3-[6-(1-methylethyl)-4-oxo-4H-quinazolin-3-yl]-2-propenoic acid and 1.445 g. (0.0088 mol) of N-methyl-3-pyridine butanamine [H. Erdtman, F. Haglid and I. Wellings, Acta Chem. Scand., 17, 1717 (1963)] in 20 ml. of anhydrous DMF cooled at 0° was added dropwise 1.9 ml (0.0088 mol) of diphenylphosphoryl azide followed by the dropwise addition of 2.5 ml. (0.0176 mol) of triethylamine. The reaction mixture was stirred at 0° for 2 hours and then at 25° for 16 hours. The DMF was removed in vacuo and $CH_2Cl_2$ (100 ml.) was added to the residue. The solution was washed with saturated $NaHCO_3$ solution, washed with water, dried ($Na_2SO_4$) and concentrated in vacuo. Chromatography of the residue on 200 g. of silica gel and elution with a solvent mixture of $CH_2Cl_2$ (190): 95% $CH_3OH(10)$: conc. $NH_4OH$ (0.1) gave 1.66 g. of solid. This as dissolved in $CH_2Cl_2$ and converted to the hydrochloride salt by the addition of 2.0 ml. of 6N HCl in $CH_3OH$. The solvent was removed in vacuo and the residue was crystallized from $CH_2Cl_2$—$Et_2O$ to yield 1.1 g. (28% yield), m.p. 61°–62°, of the above-captioned product.

EXAMPLE 5

(E)-3-[6-(1-methylethyl)-4-oxo-4H-quinazolin-3-yl]-N-[4-(3-pyridinyloxy)butyl]-2-propenamide hydrochloride A mixture of 2.066 g. (0.008 mol) of (E)-3-[6-(1-methylethyl)-4-oxo-4H-quinazolin-3-yl]-2-propenoic acid and 15 ml. of thionyl chloride was stirred at reflux for 2 hours. The excess thionyl chloride was removed in vacuo to give the solid acid chloride which was dissolved in 50 ml. of anhydrous DMF. This solution was stirred at 25° during the dropwise addition of 1.66 g (0.01 mol) of 4-(3-pyridyloxy) butanamine in 15 ml. of anhydrous DMF over 30 minutes. The solution was left at 25° for 18 hours and then was concentrated in vacuo to remove the DMF. The residue was dissolved in $CH_2Cl_2$, washed with saturated $NaHCO_3$, washed with water, dried ($Na_2SO_4$), and the $CH_2Cl_2$ layer was concentrated in vacuo to give an oil. Chromatography on 250 g. of silica gel and elution with 7% $CH_3OH$—$CH_2Cl_2$ gave 1.70 g. of an oil. This was dissolved in $CH_2Cl_2$ and converted to the hydrochloride salt by the addition of 1.0 ml. of 6N HCl in $CH_3OH$. After concentration in vacuo, the residue was crystallized from 2-propanolether to give 1.83 g. (50% yield), m.p. 89°–90°, of the above captioned product.

The 4-(3-pyridinyloxy)-1-butanamine used as a starting material above can be prepared as follows:

4-(3-pyridinyloxy)butyronitrile

Sodium hydride (13.3 g., 0.32 mol, 57% oil dispersion) was washed with pentane to remove the oil and 26.1 g. (0.275 mol) of 3-hydroxypyridine in 300 ml. of anhydrous DMF was added with cooling in a cold water bath. The mixture was then stirred and heated at 60° for 1 hour. After cooling to 25°, 40.7 g. (0.275 mol) of 4-bromobutyronitrile in 40 ml. of anhydrous DMF was added dropwise over 1 hour with cooling to keep the reaction temperature below 30°. The reaction mixture was then stirred at 25° for 17 hours and the solvent was removed in vacuo. The residue was treated with 100 ml. of water and the product was extracted with $CH_2Cl_2$. After washing the extract with 1N NaOH and then with $H_2O$, it was dried ($MgSO_4$) and concentrated in vacuo to an oil which was distilled to yield 25.1 g., b.p. 133°–135°/0.4 mm, (56% yield), of 4-(3-pyridinyloxy)butyronitrile.

4-(3-pyridinyloxy)-1-butanamine

To 2.9 g (0.073 mol) of lithium aluminum hydride stirred at 25° in 100 ml of anhydrous ether at 25° was added dropwise 4.7 g (0.029 mol) of 4-(3-pyridinyloxy)butyronitrile in 30 ml of ether and 20 ml anhydrous THF over 15 minutes. The reaction mixture was then stirred at reflux for 3.5 hours, cooled in an ice bath during the addition of 3 ml of $H_2O$, followed by 3 ml of 15% NaOH solution and finally 9 ml of $H_2O$. The granular solid was filtered, washed with $CHCl_3$ and the filtrate was concentrated in vacuo. The residue was dissolved in $CHCl_3$, washed with $H_2O$, dried ($MgSO_4$) and concentrated in vacuo to an oil. Distillation gave 2.6 g., b.p. 103°–107°/0.5 mm (53% yield) of the desired amine which was analyzed as the dihydrochloride obtained from 2-propanol-ether, m.p. 127°–131°.

EXAMPLE 6

N-[4-(1H-imidazol-1-yl)butyl]-(E)-3-[6-(1-methylethyl)-4-oxo-4H-quinazolin-3-yl]-2-propenamide The acid chloride was prepared from 2.58 g. (0.01 mol) of (E)-3-[6-(1-methylethyl)-4-oxo-4H-quinazolin-3-yl]-2-propenoic acid by refluxing with 20 ml. of thionyl chloride for 1.5 hour. The excess thionyl chloride was removed in vacuo to yield the solid acid chloride. This was dissolved in 75 ml. of anhydrous DMF and cooled to 10°. To this stirred solution was added 0.73 ml. (0.01 mol) of triethylamine followed by 1.53 g. (0.011 mol) of (1H-imidazol-1-yl)butanamine in 15 ml. of anhydrous DMF added dropwise over 30 minutes. The reaction mixture was allowed to warm to 25° and stirred for 17 hours. The DMF was removed in vacuo and the residue was treated with 150 ml. of saturated $NaHCO_3$ solution and 150 ml. of $CH_2Cl_2$. The aqueous phase was extracted with $CH_2Cl_2$ and the combined extract was washed with water, dried ($Na_2SO_4$), and concentrated in vacuo to yield a solid (3.3 g.). Purification was accomplished by chromatography on 200 g. of silica gel. Elution with a solvent mixture of $CH_2Cl_2(90):95\%$ $CH_3OH(10)$:conc. $NH_4OH(1)$ gave 1.76 g. of solid which was crystallized three times from $CH_2Cl_2$ to give 0.68 g. (18% yield), m.p. 170°–171°, of the above-captioned product.

EXAMPLE 7

Preparation of (1H-imidazol-1-yl)butanamine for use in Example 6 above

A solution of 10.8 g of (1H-imidazol-1-yl)butanenitrile in 225 ml of methanol and 2.5 ml of triethylamine was hydrogenated over 2.5 g of Raney-Cobalt at 90° C. and a hydrogen pressure of 1000 psi. The crude product obtained after filtration and concentration was distilled to give 7.8 g (70%) of (1H-imidazol-1-yl)butanamine, bp 100°–103° C./0.1 mm. The dihydrochloride salt was crystallized from ethanol, mp 139°–141° C.

EXAMPLE 8

(E)-3-[6-(1-methylethyl)-4-oxo-4H-quinazolin-3-yl]-N-[2-(4-pyridinylthio)-ethyl]-2-propenamide The acid chloride was prepared from 1.94 g. (0.0075 mol) of (E)-3-[6-(1-methylethyl)-4-oxo-4H-quinazolin-3-yl]-2-propenoic acid by refluxing with 25 ml. of thionyl chloride for 2.5 hours. The excess thionyl chloride was removed in vacuo to yield solid acid chloride. This was dissolved in 100 ml. of refluxing anhydrous toluene and 1.16 g (0.0075 mol) of 2-(4-pyridylthio)ethanamine [I. Kh. Fel'dman and A. V. Voropaeva, Tr. Leningr. Khim-Farmatsevt. Inst., 16, 17(1962)] in 50 ml of anhydrous toluene was added dropwise over 10 minutes. The reaction mixture was stirred at reflux for 3 hours and then concentrated in vacuo to dryness. Saturated $NaHCO_3$ (250 ml.) and $CH_2Cl_2$ (150 ml.) were added and the aqueous layer was extracted again with $CH_2Cl_2$. The combined extract was washed with $H_2O$, dried ($Na_2SO_4$) and concentrated in vacuo to yield a solid (3.0 g.) which was purified by liquid chromatography using 2% $CH_3OH—CH_2Cl_2$ for elution to yield 1.27 g. Recrystallization from $CH_2Cl_2$ gave 1.12 g. (34% yield), m.p. 164°–165°, of the above-captioned product.

EXAMPLE 9

(E)-3-[6-(1-methylethyl)-4-oxo-4H-quinazolin-3-yl]-N-[4-(2-pyridinyl)-butyl]-2-propenamide hydrochloride The acid chloride was prepared from 2.08 g. (0.00805 mol) of (E)-3-[6-(1-methylethyl)-4-oxo-4H-quinazolin-3-yl]-2-propenoic acid and 25 ml. of thionyl chloride as described in previous examples. The acid chloride was dissolved in 100 ml. of anhydrous DMF and cooled in an ice bath. To this solution at 5° was added dropwise with stirring 1.33 g. (0.0089 mol) of 2-pyridinebutanamine [J. W. Black and M. E. Parsons, U.S. Pat. No. 4,000,302 (1976)] in 20 ml. of anhydrous DMF over 10 minutes. The reaction mixture was allowed to warm slowly to 25° and stirred for 17 hours. An additional 0.50 g. of 2-pyridine butanamine was added and stirring was continued for 24 hours. The DMF was removed in vacuo and 100 ml. of saturated $NaHCO_3$ and 150 ml. of $CH_2Cl_2$ were added to the residue. The $CH_2Cl_2$ extract was washed with 5% $NaHCO_3$ solution, with $H_2O$, dried (Na$_2$SO$_4$), and concentrated in vacuo to a solid which was purified by liquid chromatography. Elution with 10% CH$_3$OH—CH$_2$Cl$_2$ gave 1.65 g. which was dissolved in CH$_2$Cl$_2$ and converted to the hydrochloride salt by the addition of 0.93 ml. (0.0047 mol) of 5N HCl in CH$_3$OH. The solution was concentrated in vacuo and the residue was recrystallized from 2-propanol-ether to give 1.90 g. (54% yield), m.p. 101°–102°, of the above captioned product.

EXAMPLE 10

(E)-3-[6-(1-methylethyl)-4-oxo-4H-quinazolin-3-yl]-N-[2-[[(2-pyridinyl)methyl]amino]ethyl]-2-propenamide To a stirred suspension of 1.51 g. (0.0058 mol) of (E)-3-[6-(1-methylethyl)-4-oxo-4H-quinazolin-3-yl]-2-propenoic acid and 1.06 g. (0.007 mol) of N-(2-pyridinylmethyl)-1,2-ethandiamine [E. Hoyer, Chem. Ber., 93, 2475 (1960)] in 70 ml. of anhydrous DMF cooled at −19° was added dropwise 1.5 ml. (0.007 mol) of diphenylphosphoryl azide in 5 ml. of anhydrous DMF was added dropwise over 45 minutes. The reaction mixture was stirred at −19° for 2 hours and then allowed to warm slowly to −7°. After stirring at −7° for 16 hours, the DMF was removed in vacuo. The residue was dissolved in CH$_2$Cl$_2$ and the solution was washed with saturated NaHCO$_3$ solution, with H$_2$O, dried (MgSO$_4$) and concentrated in vacuo to an oil. Purification was accomplished by chromatography on 200 g. of silica gel. Elution with a solvent mixture of CH$_2$Cl$_2$(90):95% CH$_3$OH(10):conc. NH$_4$OH(1) gave 0.63 g. of a foam which was triturated with ether to give 0.54 g., m.p. 91°–95°. Recrystallization from CH$_2$Cl$_2$-EtO$_2$ gave 0.27 g., m.p. 113°–116° of the above-captioned product.

The mother liquor from the recrystallization was purified bypreparative tlc on silica gel followed by crystallization from CH$_2$Cl$_2$—Et$_2$O to give an additional 0.12 g., m.p. 114°–118°, of product. The combined yield is thus 17%.

EXAMPLE 11

(E)-3-[6-(1-methylethyl)-4-oxo-4H-quinazolin-3-yl]-N-[2-[[(3-pyridinyl)methyl]amino]ethyl]-2-propenamide To a stirred suspension of 1.51 g. (0.0058 mol) of (E)-3-[6-(1-methylethyl)-4-oxo-4H-quinazolin-3-yl]-2-propenoic acid and 1.06 g. (0.007 mol) of N-(3-pyridinylmethyl)-1,2-ethandiamine [E. Hoyer, Chem. Ber. 93, 2475 (1960)] in 70 ml. of anhydrous DMF cooled at −18° was added dropwise 1.5 ml. (0.007 mol) of diphenylphosphoryl azide in 5 ml. of anhydrous DMF over 15 minutes. Then 1.7 mol (0.012 mol) of triethylamine in 5 ml. of anhydrous DMF was added dropwise over 15 minutes. The reaction mixture was stirred at −18° for 2.5 hours and then allowed to warm slowly to −8° and stirred at this temperature for 18 hours. After 24 hours at 25°, the DMF was removed in vacuo and the residue was dissolved in CH$_2$Cl$_2$. The solution was washed with saturated NaHCO$_3$ solution, with H$_2$O, dried (MgSO$_4$) and concentrated in vacuo to an oil. Chromatography on 200 g. of silica gel and elution with a solvent mixture of CH$_2$Cl$_2$(90):95% CH$_3$OH(10):conc. NH$_4$OH(1) gave 0.40 g. which was crystallized from CH$_2$Cl$_2$—Et$_2$O and then twice from EtOAc-hexane to yield 0.14 g., m.p. 121°–124°, of the above-captioned product.

EXAMPLE 12

(E)-3-[6-(1-methylethyl)-4-oxo-4H-quinazolin-3-yl]-N-[3-(2-pyridinylamino)propyl]-2-propenamide The acid chloride was prepared from 1.0 g. (0.0039 mol) of (E)-3-[6-(1-methylethyl)-4-oxo-4H-quinazolin-3-yl]-2-propenoic acid and 20 ml. of thionyl chloride as previously described. To the acid chloride stirred at reflux in 20 ml. of anhydrous toluene was added dropwise 0.88 g. (0.0058 mol) N-(2-pyridinyl)-1,3-propandiamine [F. C. Whitmore, H. S. Mosher, D. P. J. Goldsmith and A. W. Rytina, J. Amer. Soc. 67, 393 (1945)] in 10 ml. of anhydrous toluene over 30 minutes. The reaction mixture was stirred at reflux for 4 hours, cooled to 25°, and the resultant solid was filtered. Treatment of the brown solid with saturated NaHCO$_3$ solution and extraction with CH$_2$Cl$_2$ gave the crude product as the free base after concentration. Chromatography on 50 g. of silica gel and elution with a solvent mixture of CH$_2$Cl$_2$(190):95% CH$_3$OH(10):conc. NH$_4$OH(0.1) gave 0.73 g. which was recrystallized from ethyl acetate-hexane to give 0.61 g., m.p. 156°–159°, (40% yield), of the above-captioned product.

EXAMPLE 13

(E)-3-[6-(1-methylethyl)-4-oxo-4H-quinazolin-3-yl]-N-[6-(2-pyridinylamino)hexyl]-2-propenamide The acid chloride was prepared from 2.0 g. (0.0078 mol) of (E)-3-[6-(1-methylethyl)-4-oxo-4H-quinazolin-3-yl]-2-propenoic acid and 30 ml. of thionyl chloride as previously described. To the acid chloride stirred at reflux in 30 ml. of anhydrous toluene was added dropwise 2.2 g. (0.0116 mol) of N-(2-pyridinyl)-1,6-hexandiamine [F. C. Whitmore, H. S. Mosher, D. P. J. Goldsmith and A. W. Rytina, J. Amer. Chem. Soc., 67, 393 (1945)] in 10 ml. of anhydrous toluene over 30 minutes. The reaction mixture was stirred at reflux for 2 hours, cooled to 25°, and the resultant solid was filtered. Treatment of the dark solid with saturated NaHCO$_3$ solution and extraction with CH$_2$Cl$_2$ gave the crude product as the free base after concentration. Chromatography on 150 g. of silica gel and elution with a solvent mixture of CH$_2$Cl$_2$(190):95% CH$_3$OH(10):conc. NH$_4$OH(0.1) gave 1.54 g. which was recrystallized from CH$_2$Cl$_2$—Et$_2$O to provide 1.29 g., m.p. 120°–124°, (38% yield), of the above-captioned product.

EXAMPLE 14

(E)-3-[6,8-bis(1-methylethyl)-4-oxo-4H-quinazolin-3-yl]-N-[4-(3-pyridinyl)butyl]-2-propenamide hydrochloride To a stirred suspension of 1.18 g. (0.0039 mol) of (E)-3-[6,8-bis(1-methylethyl)-4-oxo-4H-quinazolin-3-yl]-2-propenoic acid and 0.71 g. (0.0047 mol) of 3-pyridine butanamine in 15 ml. of anhydrous DMF cooled at −5° was added 1.30 g. (0.0047 mol) of diphenylphosphoryl azide dropwise followed by 1.3 ml. (0.0094 mol) of triethylamine also added dropwise. The reaction mixture was stirred at 0° for 9 hours and at 25° for 8 hours. The solvent was removed in vacuo and the residue was dissolved in $CH_2Cl_2$ and washed with saturated $NaHCO_3$, dried ($Na_2SO_4$) and concentrated in vacuo to an oil. Chromatography on 200 g. of silica gel and elution with a solvent mixture of $CH_2Cl_2(190):95\%$ $CH_3OH(10)$:conc. $NH_4OH(0.1)$ gave a colorless solid which was dissolved in $CH_2Cl_2$ and converted to the hydrochloride salt by the addition of 0.25 ml. of 6.5N HCl in $CH_3OH$. After concentration in vacuo, the residue was crystallized from 2-propanol-ether to yield 0.66 g. (35% yield), m.p. 170°–171°, of the above-captioned product.

EXAMPLE 15

(E)-3-[6-(1-methylethyl)-4-oxo-4H-3-quinazolinyl]-N-[6-(3-pyridinyl)hexyl]-2-propenamide A mixture of 2.4 g (0.009 mol) of (E)-3-[6-(1-methylethyl)-4-oxo-4H-quinazolin-3-yl]-2-propenoic acid and 40 ml of thionyl chloride was stirred at reflux for 2 hours. The excess thionyl chloride was removed in vacuo to yield the acid chloride as a solid which was dissolved in 120 ml of refluxing anhydrous toluene. This solution was stirred at reflux during the dropwise addition of 2.47 g (0.014 mol) of 3-pyridine hexanamine in 20 ml of anhydrous toluene over 10 minutes. The mixture was stirred at reflux for 5 hours and then the solvent was removed. The residue was dissolved in $CH_2Cl_2$, washed with $NaHCO_3$ solution, washed with water, dried ($Na_2SO_4$) and the $CH_2Cl_2$ was removed in vacuo. The residue was purified by liquid chromatography using a solvent mixture of 2.5% methanol, 0.5% triethylamine-ethyl acetate to yield 0.94 g. (24% yield), m.p. 132°–133°, of the above captioned product.

EXAMPLE 16

(E)-3-(6,7-dimethyl-4-oxo-4H-quinazolin-3-yl)-N-[4-(3-pyridinyl)butyl]-2-propenamide The acid chloride is prepared from (E)-3-(6,7-dimethyl-4-oxo-4H-quinazolin-3-yl]-2-propenoic acid and thionyl chloride as previously described. When this acid chloride is allowed to react with 3-pyridine butanamine under the usual conditions, (E)-3-(6,7-dimethyl-4-oxo-4H-quinazolin-3-yl)-N-[4-(3-pyridinyl)butyl]-2-propenamide is obtained.

EXAMPLE 17

Preparation of 6-(3-pyridinyl)hexanenitrile

A solution of 62.82 g of 6-(3-pyridinyl)-5-hexynenitrile in 500 ml of 2-propanol was hydrogenated over 3.0 g of 10% palladium on carbon at atmospheric pressure. Two additional 3.0 g charges of catalyst were added as the rate of hydrogen uptake slowed. After two days, the reaction mixture was filtered, concentrated, the residue was evaporatively distilled and the distillate was dissolved in 300 ml of 2-propanol and was reduced over 3.0 g of 10% palladium on carbon. Filtration, evaporation, and distillation gave 52.15 g (82%) of 6-(3-pyridinyl)hexanenitrile, bp 150°/0.3 mm which gave a main peak consisting of 93% of the total by gas chromatography analysis. A portion was further purified by silica gel chromatography eluting with 1:1 ethyl acetate-hexane containing 1% triethyl amine and was evaporatively distilled to give an analytical sample.

EXAMPLE 18

Preparation of 3-Pyridinehexanamine

A solution of 52.15 g of 3-pyridinehexanenitrile in 600 ml of methanol and 13 ml of triethylamine was hydrogenated over 13 g of Raney cobalt at an initial hydrogen pressure of 1000 psi and 100° C. The cooled mixture was filtered and concentrated. The residue was distilled to give 46.5 g (87%) of 3-pyridinehexanamine, bp 102°–107° C./0.2 mm. This material was purified through its phthalimide which was formed by reaction with 39.53 g of phthalic anhydride in 300 ml of glacial acetic acid at reflux overnight. The residue obtained after evaporation of the solvent was dissolved in 300 ml of ethyl acetate, washed with dilute sodium hydroxide and sodium bicarbonate, dried over potassium carbonate and concentrated. The residue was crystallized from ethyl acetate-hexane to give 62.87 g (77%) of 2-[6-(3-pyridinyl)hexyl]-1H-isoindole-1,3(2H)-dione, mp 89°–92° C. A solution of this material in 880 ml of ethanol and 33 ml of hydrazine hydrate was heated to reflux for 3 hours. The cooled mixture was filtered and concentrated. The residue was taken up in 500 ml of dichloromethane and was washed with 10% sodium hydroxide and dried over potassium carbonate. The residue obtained after concentration was distilled to give 31.6 g (60% based on starting nitrile) of 3-pyridinehexanamine, bp 140°–150° C./0.3 mm which gave a single peak on gas chromatography.

EXAMPLE 19

Preparation of 2-[[(4-pyridyl)methyl]thio]ethanamine 34.1 g of sodium hydroxide was dissolved in 500 ml of ethanol under an argon atmosphere and 48.6 g of 2-mercaptoethanamine hydrochloride and 35 g of 4-chloromethylpyridine pyridine hydrochloride were added with ice bath cooling. The reaction mixture was allowed to warm to room temperature over 2 hours, was concentrated, diluted with 300 ml of water and was extracted with 3×150 ml of dichloromethane. The combined organic layers were washed with 100 ml of saturated brine, dried over potassium carbonate and were evaporated to a dark oil which was distilled. The fractions bp 120°–130° C./0.1 mm amounted to 30.68 g (85%) of 2-[[(4-pyridyl)methyl]thio]ethanamine.

EXAMPLE 20

Preparation of (E)-3-[6-(1-methylethyl)-4-oxo-4H-quinazolin-3-yl]-N-[2-(4-pyridinyl)ethyl]-2-propenamide A suspension of 2.8 g of (Z)-3-[6-(1-methylethyl)-4-oxo-4H-quinazolin-3-yl]-2-propenoic acid in 30 ml of thionyl chloride was stirred at reflux for 2.5 hours when complete solution was attained. The excess thionyl chloride was removed in vacuo to give the acid chloride as a yellow solid which was dissolved in 25 ml of anhydrous dimethyl formamide. To this solution, stirred at 0° C. was added 1.59 g of 4-(2-aminoethyl) pyridine. The mixture was stirred at 0° C. for 1.75 hours and poured into cold saturated sodium bicarbonate solution. The product was extracted with methylene chloride and the extract was washed with water. The dried (over magnesium sulfate) extract was purified by flash chromatography. Elution with 10% triethylamine and 1% methanol-methylenechloride gave a semi-solid which was crystalized from acetone to yield 522 mg, mp 141–144; (13%) of the above-captioned compound.

EXAMPLE 21

Preparation of
(E)-3-[6-(1-methylethyl)-4-oxo-4H-quinazolin-3-yl]-N-2-(2-pyridinyl)ethyl-2-propenamide A suspension of 2.5 g of (E)-3[6-(1-methylethyl)-4-oxo-4H-quinazolin-3-yl]-2-propenoic acid in 30 ml of thionyl chloride was stirred at reflux for 2.5 hours when complete solution was attained. The excess thionyl chloride was removed in vacuo to give the acid chloride as a yellow solid which was dissolved in 35 ml of anhydrous dimethylformamide. To this solution stirred at −5° C. was added 1.5 g of 2-(2-aminoethyl) pyridine. The mixture was stirred at 0° C. for 1.75 hours and poured into cold saturated sodium bicarbonate solution. The product was extracted with methylene chloride and the extract was washed with water. The dried (over magnesium sulfate) extract was purified by column chromatography. Elution with 10% triethylaminemethylene chloride gave a gray solid which was crystallized from ethyl acetate and then from isopropyl alcohol to yield 840 mg, mp 168–170 (26% yield) of the above-captioned compound.

EXAMPLE 22

| Item | TABLET FORMULATION (Wet granulation) Ingredient | mg/tablet | mg/tablet | mg/tablet |
|---|---|---|---|---|
| 1. | (E)—3-[6-(1-methylethyl-4-oxo-4H—quinazolin-3-yl]-N—[4-(3-pyridinyl)butyl]-2-propenamide hydrochloride | 100 | 250 | 500 |
| 2. | Lactose | 98.5 | 147.5 | 170 |
| 3. | Polyvinyl pyrrolidone | 15 | 30 | 40 |
| 4. | Modified starch | 15 | 30 | 40 |
| 5. | Corn starch | 15 | 30 | 40 |
| 6. | Magnesium stearate | 1.5 | 2.5 | 5 |
| | Weight of tablet | 245 mg | 490 mg | 795 mg |

PROCEDURE (1) Mix items 1, 2, 4 and 5 in a suitable mixer, granulate with polyvinyl pyrrolidone and dissolve in water/alcohol. Dry the granulation. Mill the dry granulation through a suitable mill.

(2) Add magnesium stearate and compress on a suitable press.

EXAMPLE 23

| Item | TABLET FORMULATION (Wet granulation) Ingredient | mg/tablet | mg/tablet | mg/tablet |
|---|---|---|---|---|
| 1. | (E)—-3-[6-(1-methylethyl-4-oxo-4H—quinazolin-3-yl N—[4-(3-pyridinyl)butyl]-2-propenamide hydrochloride | 100 | 250 | 500 |
| 2. | Lactose | 147.5 | 100 | 97.5 |
| 3. | Pregelatinized starch | 25 | 30 | 60 |
| 4. | Modified starch | 25 | 50 | 60 |
| 5. | Corn starch | 25 | 50 | 60 |
| 6. | Magnesium stearate | 2.5 | 5 | 7.5 |
| | Weight of tablet | 325 mg | 500 mg | 785 mg |

PROCEDURE (1) Mix items 1, 2, 3, 4 and 5 in a suitable mixer, granulate with water, and dry over night in a suitable oven. Mill through suitable mill.

(2) Mix with item 6 and compress on a suitable press.

EXAMPLE 24

| Item | CAPSULE FORMULATION Ingredient | mg/capsule | mg/capsule | mg/capsule |
|---|---|---|---|---|
| 1. | (E)—3[6-(1-methylethyl-4-oxo-4H—quinazolin-3-yl N—[4-(3-pyridinyl)butyl-2-propenamide hydrochloride | 100 | 250 | 500 |
| 2. | Lactose | 99 | 148 | — |
| 3. | Corn starch | 20 | 30 | 57 |
| 4. | Talc | 5 | 10 | 15 |
| 5. | Magnesium stearate | 1 | 2 | 3 |
| | Fill weight of capsule | 225 mg | 440 mg | 575 mg |

PROCEDURE (1) Mix items 1, 2 and 3 in a suitable mixer. Mill through a suitable mill.
(2) Mix the mixture in Step 1 with items 4 and 5 and fill on a suitable machine.

We claim:

1. A compound of the formula

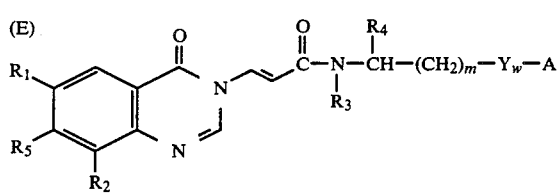

wherein $R_1$ is hydrogen, lower alkyl, lower cycloalkyl, lower alkoxy, hydroxy, halo, lower alkylthio, lower alkylsulfinyl, lower alkylsulfonyl, di($C_1$-$C_7$)alkyl-N($CH_2$)$_n$O-or 2-hydroxyethoxy; n is 2 to 7; $R_2$ is hydrogen, lower alkyl or lower alkoxy; $R_3$ is hydrogen or methyl; $R_4$ is hydrogen or lower alkyl; $R_5$ is hydrogen or lower alkyl provided however if $R_2$ is other than hydrogen $R_5$ is hydrogen; m is 1 to 7; Y is

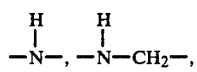

—O—, or —S—; w is zero or one; and A is 1,2,4-triazinyl or an aromatic 5- or 6-membered hetrocyclic radical having 1 to 2 hetero-atoms which may be the same or different and are selected from the group consisting of nitrogen oxygen and sulfur, and wherein the 3-pyridinyl radical may have an N-methyl group;

or a pharmaceutically acceptable addition salt thereof.

2. A compound, of claim 1, wherein —$Y_w$—A is selected from the group consisting of

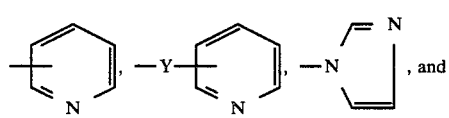, and

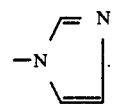

3. A compound, of claim 2, wherein $R_1$ is lower alkyl and $R_2$ is hydrogen.

4. A compound, of claim 3, wherein $R_1$ is isopropyl.

5. A compound of claim 4, wherein $Y_w$—A is

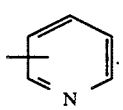

6. A compound in accordance with claim 5, (E)-3-[6-(1-methylethyl)-4-oxo-4H-quinazolin-3-yl]-N-[4-(3-pyridinyl)butyl]-2-propenamide or a salt thereof.

7. A compound in accordance with claim 5, (E)-3-[6-(1-methylethyl)-4-oxo-4H-quinazolin-3-yl]-N-[4-(2-pyridinyl)butyl]-2-propenamide or a salt thereof.

8. A compound in accordance with claim 5, (E)-N-methyl-3-[6-(1-methylethyl)-4-oxo-4H-quinazolin-3-yl]-N-[4-(3-pyridinyl)butyl)]-2-propenamide.

9. A compound, of claim 4, wherein —$Y_w$—A is

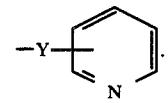

10. A compound in accordance with claim 9, (E)-3-[6-(1-methylethyl)-4-oxo-4H-quinazolin-3-yl]-N-[4-(3-pyridinyloxy)butyl]-2-propenamide hydrochloride.

11. A compound in accordance with claim 9, (E)-3-[6-(1-methylethyl)-4-oxo-4H-quinazolin-3-yl]-N-[2-(4-pyridinylthio)-ethyl]-2-propenamide.

12. A compound in accordance with claim 9, (E)-3-[6-(1-methylethyl)-4-oxo-4H-quinazolin-3-yl]-N-[2-(2-pyridinylamino)propyl]-2-propenamide.

13. A compound in accordance with claim 9, (E)-3-[6-(1-methylethyl)-4-oxo-4H-quinazolin-3-yl]-N-[6-(2-pyridinylamino)hexyl]-2-propenamide.

14. A compound, of claim 4, wherein $Y_w$—A is

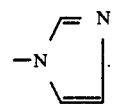

15. A compound in accordance with claim 14, N-[4-(1H-imidazol-1-yl)butyl]-(E)-3-[6-(1-methylethyl)-4-oxo-4H-quinazolin-3-yl]-2-propenamide.

16. A compound, of claim 4, wherein —$Y_w$—A is

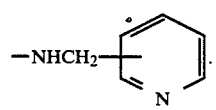

17. A compound in accordance with claim 16, (E)-3-[6-(1-methylethyl)-4-oxo-4H-quinazolin-3-yl]-N-[2-[[(2-pyridinyl)methyl]amino]ethyl]-2-propenamide.

18. A compound in accordance with claim 16, (E)-3-[6-(1-methylethyl)-4-oxo-4H-quinazolin-3-yl-N-[2-[[(3-pyridinyl)methyl]amino]ethyl]-2-propenamide.

19. A compound, of claim 2, wherein $R_1$ and $R_2$ both are lower alkyl.

20. A compound, of claim 2, wherein $R_1$ and $R_2$ both are isopropyl.

21. A compound in accordance with claim 20, (E)-3-[6,8(bis(1-methylethyl)-4-oxo-4H-quinazolin-3-yl]-N-[4-(3-pyridinyl)butyl]-2-propenamide hydrochloride.

22. A compound, of claim 2, wherein $R_1$ and $R_5$ both are lower alkyl.

23. A pharamaceutical composition comprising an anti-allergically effective amount of a compound of the formula

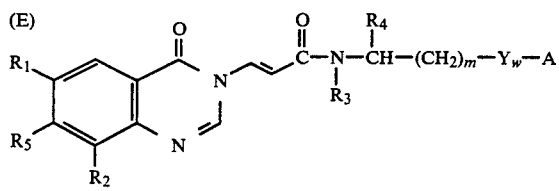

where $R_1$ is hydrogen, lower alkyl, lower cycloalkyl, lower alkoxy, hydroxy, halo, lower alkylthio, lower alkylsulfinyl, lower alkylsulfonyl, di-$(C_1-C_7)$alkyl-$N(CH_2)_nO$— or 2-hydroxyethoxy; n is 2 to 7; $R_2$ is hydrogen, lower alkyl or lower alkoxy; $R_3$ is hydrogen or methyl; $R_4$ is hydrogen or lower alkyl; $R_5$ is hydrogen or lower alkyl provided however if $R_2$ is other than hydrogen $R_5$ is hydrogen, m is 1 to 7;

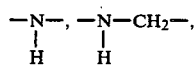

—O—, or —S—; w is zero or one; and A is 1,2,4-triazinyl or an aromatic 5- or 6-membered heterocyclic radical having 1 to 2 hetero-atoms which may be the same or different and are selected from the group consisting of nitrogen, oxygen and sulfur, and wherein the 3-pyridinyl radical may have an N-methyl group; or a pharmaceutically acceptable addition salt thereof, and an inert pharmaceutical carrier material.

24. A method of treating an allergic condition which comprises administering to a host in need thereof an effective amount of a compound of the formula

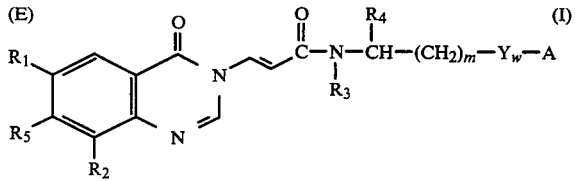

wherein $R_1$ is hydrogen, lower alkyl, lower cycloalkyl, lower alkoxy, hydroxy, halo, lower akylthio, lower alkylsulfinyl, lower alkylsulfonyl, di-$(C_1-C_7)$alkyl—$N(CH_2)_nO$— or 2-hyroxyethoxy; n is 2 to 7; $R_2$ is hydrogen, lower alkyl or lower alkoxy; $R_3$ is hydrogen or methyl; $R_4$ is hydrogen or lower alkyl; $R_5$ is hydrogen or lower alkyl provided however if $R_2$ is other than hydrogen $R_5$ is hydrogen; m is 1 to 7; Y is

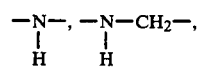

—O— or —S—; w is zero or one; and A is an aromatic 5- or 6-membered heterocyclic radical having 1 to 2 hetero-atoms which may be the same or different and are selected from the group consisting of nitrogen, oxgen and sulfur, and wherein the 3-pyridinyl radical may have an N-methyl group;

or a pharmaceutically acceptable addition salt thereof.

25. A pharmaceutical composition in accordance with claim 23, wherein —Yw—A is selected from the group consisting of

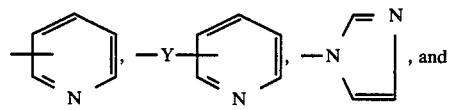

26. A pharmaceutical composition in accordance with claim 25, wherein the compound of formula I is (E)-N-methyl-3-[6-(1-methylethyl)-4-oxo-4H-quinazolin-3-yl]-N-[4-(3-pyridinyl)butyl]-2-propenamide.

27. A method in accordance with claim 24, wherein —Yw—A is selected from the group consisting of

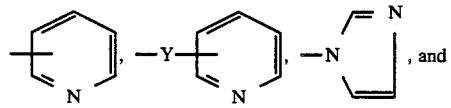

28. A method in accordance with claim 27, wherein the compound of formula I is (E)-N-methyl-3-[6-(1-methylethyl)-4-oxo-4H-quinazolin-3-yl]-N-[4-(3-pyridinyl)butyl]-2-propenamide.

* * * * *

UNITED STATES PATENT AND TRADEMARK OFFICE
CERTIFICATE OF CORRECTION

PATENT NO.   : 4,599,336
DATED        : July 8, 1986
INVENTOR(S)  : Matthew Carson et al.

It is certified that error appears in the above-identified patent and that said Letters Patent is hereby corrected as shown below:

In claim 24, column 29, line 50, delete "hyroxyethoxy" and insert therefor -- hydroxyethoxy --.

In claim 24, column 30, line 8, after the words " A is" add -- 1,2,4-triazinyl or --.

Signed and Sealed this

Twelfth Day of July, 1988

*Attest:*

DONALD J. QUIGG

*Attesting Officer*   *Commissioner of Patents and Trademarks*